United States Patent
Chiba

(10) Patent No.: US 10,426,325 B2
(45) Date of Patent: Oct. 1, 2019

(54) IMAGE CAPTURING SYSTEM AND ELECTRONIC ENDOSCOPE SYSTEM

(71) Applicant: HOYA CORPORATION, Tokyo (JP)

(72) Inventor: Toru Chiba, Tokyo (JP)

(73) Assignee: HOYA CORPORATION, Tokyo (JP)

(*) Notice: Subject to any disclaimer, the term of this patent is extended or adjusted under 35 U.S.C. 154(b) by 790 days.

(21) Appl. No.: 14/837,300

(22) Filed: Aug. 27, 2015

(65) Prior Publication Data

US 2016/0058274 A1   Mar. 3, 2016

(30) Foreign Application Priority Data

Sep. 3, 2014  (JP) .................. 2014-179036

(51) Int. Cl.
*A61B 5/00*    (2006.01)
*A61B 1/06*    (2006.01)
(Continued)

(52) U.S. Cl.
CPC .......... *A61B 1/0638* (2013.01); *A61B 1/0002* (2013.01); *A61B 1/00009* (2013.01);
(Continued)

(58) Field of Classification Search
CPC ..... A61B 1/00; A61B 1/00009; A61B 1/0638; A61B 1/0646; A61B 5/0059;
(Continued)

(56) References Cited

U.S. PATENT DOCUMENTS 5,408,998 A    4/1995  Mersch
7,892,169 B2   2/2011  Gono et al.
(Continued)

FOREIGN PATENT DOCUMENTS

CN    103070658    5/2013
CN    103654687    3/2014
(Continued)

OTHER PUBLICATIONS

US 9,560,957 B2, 02/2017, Yokouchi et al. (withdrawn)
(Continued)

*Primary Examiner* — Eric F Winakur
*Assistant Examiner* — Chu Chuan Liu
(74) *Attorney, Agent, or Firm* — Greenblum & Bernstein, P.L.C.

(57) ABSTRACT

An image capturing system, comprising: a light source device that emits illumination light containing wavelength regions; an image pickup device having an RGB filter; and an image processing unit to calculate a first index representing a molar concentration ratio of a first biological substance and a second biological substance contained in the living tissue, wherein the wavelength regions comprise: a first wavelength region corresponding to a B filter; and a second wavelength region corresponding to a G filter, wherein: in the first wavelength region, a value of image data B varies depending on the molar concentration ratio; the second wavelength region contains a plurality of isosbestic points of the living tissue, and, in the second wavelength region, a value of image data G takes a constant value without depending on the molar concentration ratio.

20 Claims, 9 Drawing Sheets

(51) Int. Cl.
*A61B 1/00* (2006.01)
*A61B 5/145* (2006.01)
*A61B 5/1455* (2006.01)
*A61B 5/1459* (2006.01)
*G06T 7/00* (2017.01)
*G01N 21/31* (2006.01)
*G01N 21/47* (2006.01)
*G01N 33/49* (2006.01)

(52) U.S. Cl.
CPC ........ *A61B 1/00186* (2013.01); *A61B 1/0646* (2013.01); *A61B 5/1459* (2013.01); *A61B 5/14546* (2013.01); *A61B 5/14551* (2013.01); *A61B 5/14552* (2013.01); *G01N 21/314* (2013.01); *G01N 21/474* (2013.01); *G06T 7/0012* (2013.01); *A61B 1/0005* (2013.01); *A61B 1/00059* (2013.01); *G01N 33/4925* (2013.01); *G01N 2021/3148* (2013.01); *G06T 2207/10068* (2013.01)

(58) Field of Classification Search
CPC ............... A61B 5/1455; A61B 5/14551; A61B 5/14552; A61B 5/1459; A61B 1/0002; A61B 1/00186; A61B 1/0005; A61B 1/00059; A61B 5/14546
See application file for complete search history.

(56) References Cited

U.S. PATENT DOCUMENTS

| | | | |
|---|---|---|---|
| 7,949,387 B2 | 5/2011 | Khoobehi et al. | |
| 8,681,208 B2 | 3/2014 | Yoshino | |
| 8,913,111 B2 | 12/2014 | Takahashi | |
| 9,277,190 B2 | 3/2016 | Igarashi et al. | |
| 9,370,297 B2 | 6/2016 | Yokouchi et al. | |
| 9,414,741 B2 | 8/2016 | Yamamoto | |
| 9,591,966 B2 | 3/2017 | Yokouchi et al. | |
| 2002/0175993 A1 | 11/2002 | Ueno et al. | |
| 2003/0060684 A1 | 3/2003 | Ayame et al. | |
| 2003/0158470 A1 | 8/2003 | Wolters et al. | |
| 2003/0176768 A1 | 9/2003 | Gono et al. | |
| 2005/0027166 A1 | 2/2005 | Matsumoto et al. | |
| 2006/0018031 A1 | 1/2006 | Takasugi | |
| 2009/0069653 A1 | 3/2009 | Yoshida et al. | |
| 2009/0137908 A1* | 5/2009 | Patwardhan ......... | A61B 5/0059 600/476 |
| 2010/0106013 A1 | 4/2010 | Morishita | |
| 2010/0168584 A1 | 7/2010 | Fujinuma et al. | |
| 2010/0331624 A1 | 12/2010 | Suzuki et al. | |
| 2011/0230715 A1* | 9/2011 | Saito ................... | A61B 5/1459 600/109 |
| 2011/0237915 A1 | 9/2011 | Yamaguchi | |
| 2011/0254937 A1 | 10/2011 | Yoshino | |
| 2012/0116159 A1 | 5/2012 | Mizuyoshi et al. | |
| 2012/0116192 A1 | 5/2012 | Saito | |
| 2012/0157768 A1* | 6/2012 | Saito .................. | A61B 5/14551 600/109 |
| 2012/0215066 A1 | 8/2012 | Akiyama et al. | |
| 2012/0302847 A1* | 11/2012 | Ozawa ................ | A61B 1/0638 600/339 |
| 2012/0327205 A1 | 12/2012 | Takahashi | |
| 2013/0039147 A1* | 2/2013 | Witte .................... | A61B 5/0093 367/7 |
| 2013/0162790 A1 | 6/2013 | Tanaka et al. | |
| 2013/0245419 A1* | 9/2013 | Oishi ................... | A61B 5/7425 600/407 |
| 2013/0289373 A1* | 10/2013 | Yamamoto ........... | A61B 5/1459 600/339 |
| 2013/0310668 A1 | 11/2013 | Young | |
| 2013/0345517 A1* | 12/2013 | Morimoto ............ | A61B 1/0661 600/178 |
| 2014/0012113 A1* | 1/2014 | Kaku ................. | A61B 5/14551 600/339 |
| 2014/0066733 A1 | 3/2014 | Saito | |
| 2014/0152790 A1 | 6/2014 | Saito et al. | |
| 2014/0185907 A1 | 7/2014 | Chiba | |
| 2014/0235973 A1 | 8/2014 | Brittenham et al. | |
| 2015/0238126 A1 | 8/2015 | Saito | |
| 2015/0238127 A1 | 8/2015 | Saito | |
| 2016/0058348 A1 | 3/2016 | Morimoto et al. | |
| 2016/0120449 A1 | 5/2016 | Chiba | |

FOREIGN PATENT DOCUMENTS

| | | |
|---|---|---|
| CN | 103654690 | 3/2014 |
| CN | 103796566 | 5/2014 |
| CN | 105324064 | 2/2016 |
| EP | 2449950 | 5/2012 |
| EP | 2468187 | 6/2012 |
| EP | 2689712 | 1/2014 |
| EP | 2702938 | 3/2014 |
| EP | 3005933 | 4/2016 |
| JP | 6-79594 | 10/1994 |
| JP | 2001-314370 | 11/2001 |
| JP | 2002-95635 | 4/2002 |
| JP | 2002-175702 | 6/2002 |
| JP | 2003-93343 | 4/2003 |
| JP | 2003-126014 | 5/2003 |
| JP | 3559755 | 9/2004 |
| JP | 3583731 | 11/2004 |
| JP | 3607857 | 1/2005 |
| JP | 2006-39043 | 2/2006 |
| JP | 2007-29453 | 2/2007 |
| JP | 2011-10998 | 1/2011 |
| JP | 2011-224038 | 11/2011 |
| JP | 2012-100800 | 5/2012 |
| JP | 2012-143348 | 8/2012 |
| JP | 2012-235962 | 12/2012 |
| JP | 2012-245223 | 12/2012 |
| JP | 2013-39215 | 2/2013 |
| JP | 2013-63097 | 4/2013 |
| JP | 5362149 | 12/2013 |
| JP | 2014-230647 | 12/2014 |
| JP | 2014-233344 | 12/2014 |
| WO | 2008/093745 | 8/2008 |
| WO | 2010/044432 | 4/2010 |
| WO | 2011/080996 | 7/2011 |
| WO | 2011/099322 | 8/2011 |
| WO | 2011/162111 | 12/2011 |
| WO | 2012/047806 | 4/2012 |
| WO | 2012/090552 | 7/2012 |
| WO | 2013/047054 | 4/2013 |
| WO | 2014/192781 | 12/2014 |

OTHER PUBLICATIONS

Office Action issued in Japan Patent Appl. No. 2012-180902, dated May 24, 2016, along with an English translation thereof.
Office Action issued in China Patent Appl. No. 201310358808.2, dated Jun. 24, 2016, along with an English translation thereof.
Office Action issued in China Patent Appl. No. 201310358808.2, dated Nov. 4, 2015, along with an English translation thereof.
Office Action issued in Japan Patent Appl. No. 2012-180902, dated Dec. 26, 2016, along with an English translation thereof.
Office Action issued in China Patent Appl. No. 201310358808.2, dated Jan. 16, 2017, along with an English translation thereof.
Extended European Search Report issued in European Patent Appl. No. 14805121.2, dated Mar. 20, 2017.
U.S. Appl. No. 15/295,048 to Fumika Yokouchi et al., which was filed Oct. 17, 2016.
International Search Reporting (ISR) in International Application PCT/JP2016/058112, dated Jun. 7, 2016.
Office Action in U.S. Appl. No. 15/295,048, dated Nov. 22, 2016.
U.S. Appl. No. 15/308,479 to Fumika Yokouchi, which was filed Nov. 2, 2016.
Office Action issued in European Counterpart Patent Appl. No. 15183306.8, dated Jan. 24, 2017.
Extended European Search Report issued in European Patent Appl. No. 16175262.1, dated Nov. 17, 2016.

(56) References Cited

OTHER PUBLICATIONS

Office Action issued in U.S. Appl. No. 14/936,965, dated Dec. 15, 2017.
Office Action issued in Japan Patent Appl. No. 2014-179036, dated Feb. 23, 2017.
Office Action issued in U.S. Appl. No. 15/295,048, dated Apr. 12, 2017.
U.S. Appl. No. 14/936,965 to Toru Chiba, which was filed Nov. 10, 2015.
European Search Report issued in European Patent Application No. 15195635.6, dated Apr. 18, 2016.
Office Action issued in China Patent Appl. No. 201510549104.2, dated Apr. 18, 2017, along with an english translation thereof.
Search Report issued by E.P.O. patent office in E.P.O. Patent Application No. 15183306.8, dated Feb. 5, 2016.
Office Action issued in Japan Counterpart Patent Appl. No. 2016-144055, dated Mar. 1, 2018.
Office Action issued in Japan Counterpart Patent Appl. No. 2016-144055, dated Oct. 2, 2018.
Office Action issued in U.S. Appl. No. 14/894,119, dated Jul. 8, 2019.

\* cited by examiner

IMAGE CAPTURING SYSTEM AND ELECTRONIC ENDOSCOPE SYSTEM

BACKGROUND OF THE INVENTION

The present invention relates to an image capturing system and an electronic endoscope system.

Recently, an endoscope device (a spectroscopic endoscope device) equipped with a function to capture spectral images has been proposed. With such an spectroscopic endoscope device, it may be possible to obtain image information containing spectral property (e.g. a reflectivity spectrum) of a living tissue such as a mucous membrane in a digestive organ. It is known that the reflectivity spectrum of a living tissue reflects information concerning types or densities of components contained in the vicinity of a surface layer of the subject living tissue targeted for measurement. Specifically, it is known that absorbance calculated from the reflectivity spectrum of the living tissue can be obtained by linearly superimposing absorbance of a plurality of substances which constitute the living tissue.

It is known that a living tissue in a diseased portion is different from a living tissue in a healthy portion in regard to a composition and component amounts. It is reported in prior research that abnormality of a diseased portion, represented by a cancer, is deeply related to a state of blood, namely, a state of whole blood volume and oxygen saturation. It is a frequently used manner in spectroscopic analytical chemistry to qualitatively and quantitatively analyze interesting two living tissues using spectroscopically characteristic amounts of the two living tissues in the visible light region. Therefore, it is possible to estimate whether or not a living tissue contains a diseased portion by comparing a spectral property of blood of a living tissue containing a diseased portion with a spectral property of blood of a living tissue containing only a healthy portion.

The spectral images are constituted by a plurality of image information captured with light having different wavelengths. As the wavelength information contained in the spectral image (the numbers of wavelengths used to obtained image information) increases, obtained information concerning the living tissue becomes more accurate. Japanese Patent Provisional Publication No. 2012-245223A (hereafter, referred to as patent document 1) discloses an example of a spectroscopic endoscope device which obtains spectral images at intervals of wavelength of 5 nm within a wavelength region of 400 nm to 800 nm.

SUMMARY OF THE INVENTION

However, in order to obtain spectral images with a high degree of wavelength resolution as described in patent document 1, it is necessary to capture a number of images while changing wavelength of illumination light. Furthermore, since the required calculation amount for analyzing images is larger, a long calculation time is needed for the analysis. That is, in order to obtain effective information for assisting diagnosis, it is necessary to repeatedly execute relatively complicated capturing and calculation, which requires a long time.

The present invention is advantageous in that it provides an image capturing system and an electronic endoscope system capable of obtaining, in a short time, image information representing distribution of biological substances, such as, distribution of oxygen saturation.

According to an aspect of the invention, there is provided an image capturing system, comprising: a light source device that emits illumination light containing a plurality of wavelength regions separated from each other; an image pickup device that generates image data by capturing an image of a living tissue being a subject illuminated with the illumination light, the image pickup device having an RGB filter; and an image processing unit configured to calculate a first index representing a molar concentration ratio of a first biological substance and a second biological substance contained in the living tissue based on the image data generated by the image pickup device. In this configuration, The plurality of wavelength regions comprise: a first wavelength region corresponding to a B filter of the RGB filter; and a second wavelength region corresponding to a G filter of the RGB filter. In the first wavelength region, a value of image data B of the living tissue captured by a light-receiving element of the image pickup device to which the B filter is attached varies depending on the molar concentration ratio. The second wavelength region contains a plurality of isosbestic points of the living tissue, and, in the second wavelength region, a value of image data G of the living tissue captured by a light-receiving element of the image pickup device to which the G filter is attached takes a constant value without depending on the molar concentration ratio. The image processing unit is configured to calculate the first index having correlation with the molar concentration ratio based on the image data B and the image data G.

With this configuration, it becomes possible to obtain, in a short time, image information representing distribution of biological substances, such as, distribution of oxygen saturation.

In at least one aspect, the light source device may comprises: a white light source; and an optical filter that separates the illumination light from white light emitted by the white light source.

In at least one aspect, the first index may be defined as a value obtained by dividing the image data B by the image data G.

In at least one aspect, the plurality of wavelength regions may comprise a third wavelength region corresponding to an R filter of the RGB filter. In this case, absorbance of the living tissue in the third wavelength region is regarded as almost zero, and the image processing unit is configured to calculate a second index having correlation with a sum of molar concentrations of the first biological tissue and the second biological tissue based on the image data G and image data R of the living tissue captured by a light-receiving element of the image pickup device to which the R filter is attached.

In at least one aspect, the second index may be defined as a value obtained by dividing the image data G by the image data R.

In at least one aspect, the image capturing system may further comprise a memory storing base line image data $BL_R$, $BL_G$ and $BL_B$ respectively corresponding to image data of R, G and B colors obtained by capturing a color reference plate illuminated with the illumination light.

In at least one aspect, the image processing unit may be configured to calculate the first index and the second index using, in place of the image data R, the image data G and the image data B, standardization image data $R_S$, $G_S$ and $B_S$ defined by following expressions:

$$R_S = R/BL_R$$

$$G_S = G/BL_G$$

$$B_S = B/BL_B$$

In at least one aspect, the image processing unit may be configured to generate first index image data representing distribution of the first index in the living tissue.

In at least one aspect, the first index image data may be image data having a pixel value being the first index.

In at least one aspect, the first biological substance may be oxyhemoglobin, the second biological substance may be deoxyhemoglobin, and the first index may have correlation with oxygen saturation.

In at least one aspect, the image processing unit may be configured to calculate a third index representing a degree of possibility of a malignant tumor of the living tissue based on the first index and the second index.

In at least one aspect, for a pixel having the first index lower than a first reference value and the second index higher than a second reference value, a value representing a high possibility of a malignant tumor may be assigned to the third index.

In at least one aspect, the second wavelength region may be comparted by a first pair of isosbestic points of the living tissue, and may include a second pair of isosbestic points of the living tissue lying within a range defined by the first pair of isosbestic points.

According to another aspect of the invention, there is provided an electronic endoscope system, comprising: the above described image capturing system; and an electronic scope provided with the image pickup device.

BRIEF DESCRIPTION OF THE ACCOMPANYING DRAWINGS

FIGS. 8A and 8B are examples of images generated by the electronic endoscope system according to the embodiment, in which FIG. 8A is an endoscopic image and FIG. 8B is an image of oxygen saturation distribution.

DETAILED DESCRIPTION OF THE EMBODIMENTS

Hereinafter, an embodiment according to the invention is described with reference to the accompanying drawings. In the following, an electronic endoscope system is explained as an embodiment of the invention by way of example.

The electronic endoscope system according to the embodiment explained below quantitatively analyzes biological information (e.g., oxygen saturation and blood volume) of a subject based on a plurality of images (three primary color images of R, G, B constituting one color image in this embodiment) captured using light having different wavelength regions, and the electronic endoscope system images and displays analysis results. In the quantitative analysis for, for example, oxygen saturation, explained below using the electronic endoscope system according to the embodiment, a characteristic where a spectral property of blood in a visible light region continuously changes depending on oxygen saturation is utilized.

Calculation Principle of Spectral Property of Hemoglobin and Oxygen Saturation Before explaining in detail a configuration of the electronic endoscope system according to the embodiment of the invention, a calculation principle of the spectral property of hemoglobin in a visible light region and oxygen saturation according to the embodiment is explained.

Figure 1:
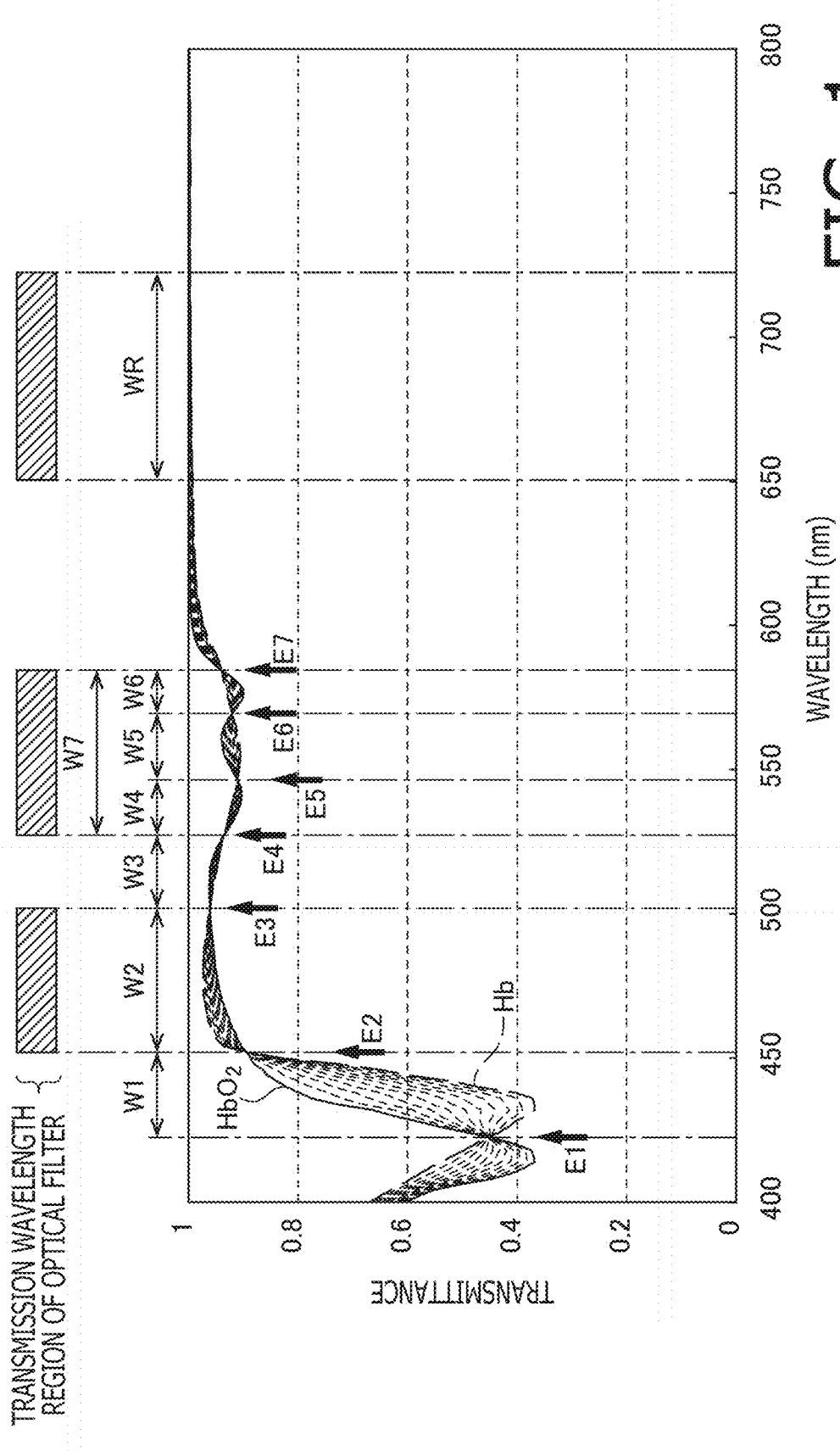
FIG. 1 illustrates a transmittance spectrum of hemoglobin.

FIG. 1 illustrates a transmittance spectrum of hemoglobin. The spectral property of hemoglobin changes depending on oxygen saturation (a ration of oxyhemoglobin with respect to total hemoglobin). A waveform indicated by a solid line in FIG. 1 represents a transmittance spectrum in the case of oxygen saturation of 100% (i.e., oxyhemoglobin $HbO_2$), and a waveform indicated by a long dashed line represents a transmittance spectrum in the case of oxygen saturation of 0% (i.e., deoxyhemoglobin Hb). Further, a waveform indicated by a short dashed line represents a transmittance spectrum of hemoglobin (a mixture of oxyhemoglobin and deoxyhemoglobin) at an intermediate oxygen saturation (10%, 20%, 30%, ... 90%).

The absorbance A of hemoglobin is calculated from light transmittance T by the following equation (1):

$$A = -\log T \quad (1)$$

Since the transmittance spectrum of hemoglobin shown in FIG. 1 is an optical spectrum of two components where the total density of respective components (oxyhemoglobin and deoxyhemoglobin) takes a constant value, isosbestic points E1 (424 nm), E2 (452 nm), E3 (502 nm), E4 (528 nm), E5 (546 nm), E6 (570 nm) and E7 (584 nm) appear. At each of the isosbestic points, the absorbance A (i.e., the transmittance T) takes a constant value without depending on a density ratio (i.e., oxygen saturation) of respective components. In this embodiment, a wavelength region from the isosbestic point E1 to the isosbestic point E2 is defined as a wavelength region W1, a wavelength region from the isosbestic point E2 to the isosbestic point E3 is defined as a wavelength region W2, a wavelength region from the isosbestic point E3 to the isosbestic point E4 is defined as a wavelength region W3, a wavelength region from the isosbestic point E4 to the isosbestic point E5 is defined as a wavelength region W4, a wavelength region from the isosbestic point E5 to the isosbestic point E6 is defined as a wavelength region W5, and a wavelength region from the isosbestic point E6 to the isosbestic point E7 is defined as a wavelength region W6.

Figure 2:
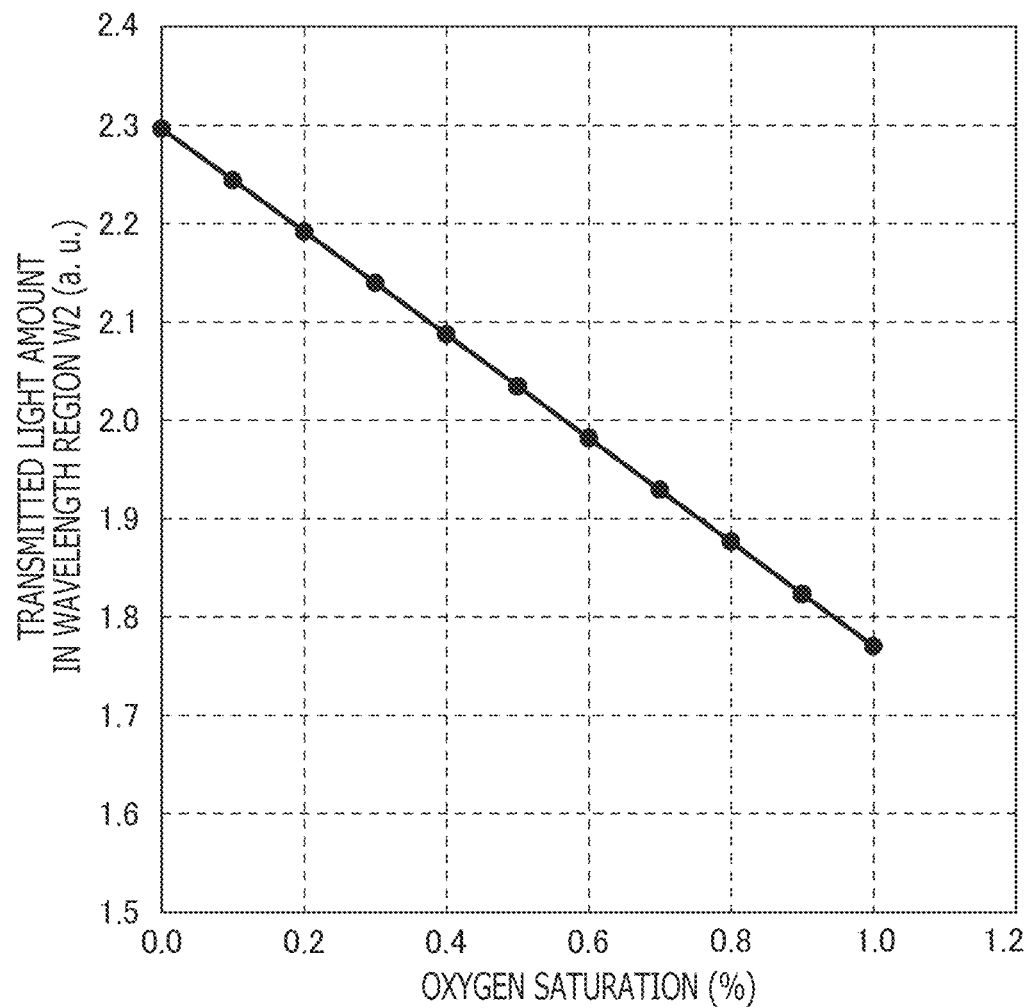
FIG. 2 is a graph plotting relationship between a transmitted light amount of blood in a wavelength region W2 and oxygen saturation.

Between the neighboring isosbestic points, the absorbance monotonously increases or decreases in accordance with increase of oxygen saturation. Furthermore, between the neighboring isosbestic points, the absorbance A of hemoglobin changes approximately linearly with respect to oxygen saturation. FIG. 2 is a graph where relationship between the transmitted light amount of blood (the vertical axis) in the wavelength region W2 and oxygen saturation (the horizontal axis) is plotted. The transmitted light amount of the vertical axis represents an integrated value within the entire wavelength region W2. From the graph of FIG. 2, it is understood that the absorbance of hemoglobin decreases approximately linearly with respect to oxygen saturation in the wavelength region W2. It should be noted that, within the neighboring wavelength region W1, the absorbance of hemoglobin increases linearly with respect to oxygen saturation. Although, to be precise, light transmittance is a changing amount which conforms to Beer-Lambert Law, the light transmittance can be regarded as changing approximately linearly within a comparatively narrow wavelength region, such as within a range of 20 nm to 80 nm.

Focusing on the wavelength region from the isosbestic point E4 to the isosbestic point E7 (i.e., a continuous wavelength region from the wavelength region W4 to W6, which is defined as a wavelength region W7 in this embodiment), the absorbance of blood increases monotonously in accordance with increase of oxygen saturation within the wavelength regions W4 and W6; however, the absorbance of blood inversely decreases monotonously within the wavelength region W5 in accordance with increase of oxygen saturation. However, the inventor of the present invention has found that the decreasing amount of absorbance of blood in the wavelength region W5 is approximately equal to the increasing amount of absorbance of blood in the wavelength regions W4 and W6, and therefore, within the whole wavelength region W7, the absorbance of blood becomes approximately constant value without depending on oxygen saturation.

Figure 3:
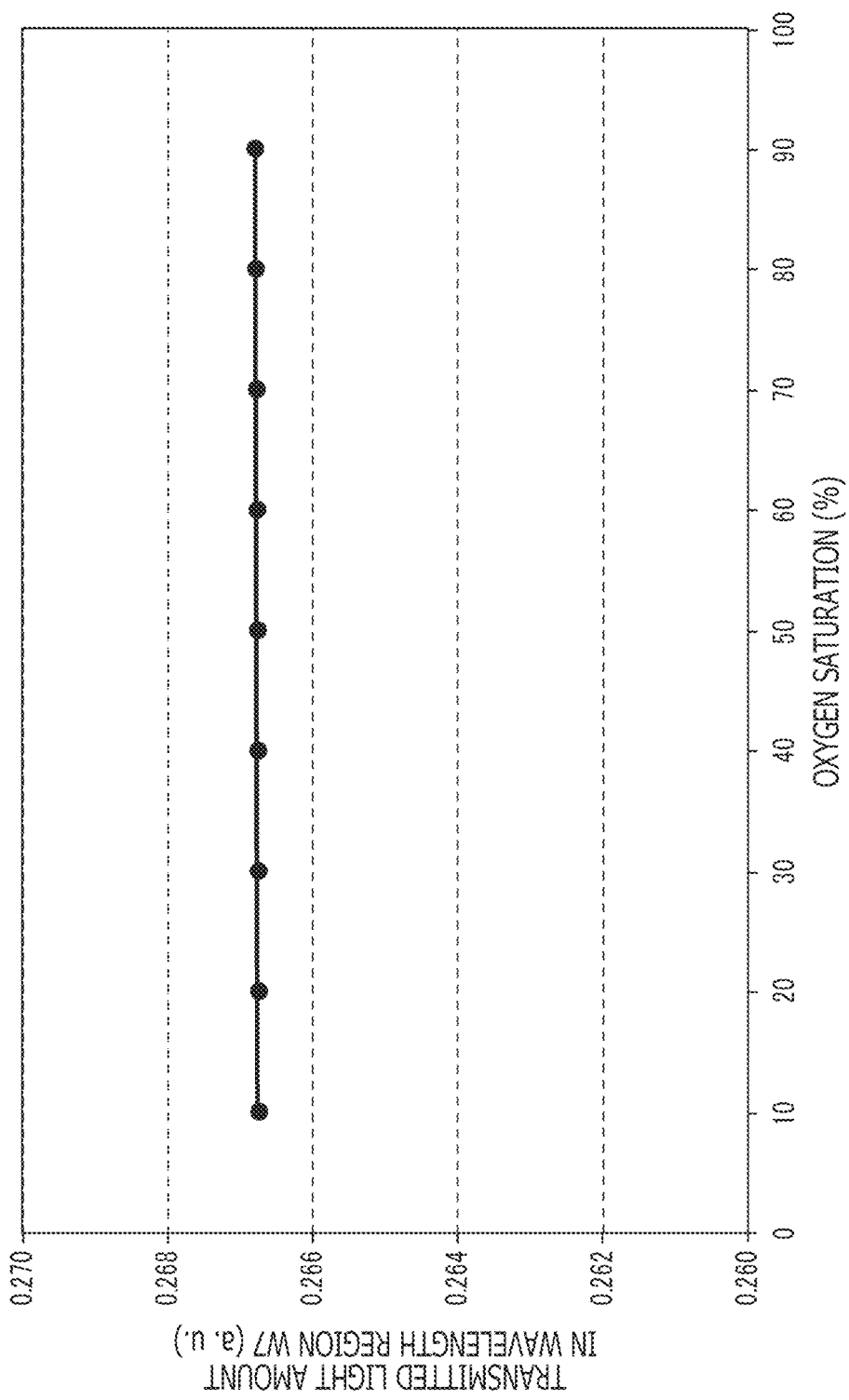
FIG. 3 is a graph plotting relationship between a transmitted light amount of blood and oxygen saturation within a wavelength region W7.

FIG. 3 is a graph in which the relationship between the transmitted light amount of blood (the vertical axis) and oxygen saturation (the horizontal axis) within the wavelength region W7 is plotted. The transmitted light amount of the vertical axis is an integrated value of the whole wavelength region W7. The average value of the transmitted light amount is 0.267 (an arbitrary unit), and the standard deviation is $1.86 \times 10^{-5}$. From FIG. 3, it is understood that, as a whole, the transmitted light amount of blood becomes approximately constant in the wavelength region W7 without depending on oxygen saturation.

Furthermore, as shown in FIG. 1, in a wavelength region larger than or equal to approximately 630 nm (in particular in a region larger than or equal to 650 nm), the absorbance of hemoglobin is small, and almost no change occurs in the light transmittance even when oxygen saturation changes. When a xenon lamp is used for a white light source, a sufficiently large amount of light can be obtained for a white light source within a wavelength region smaller than or equal to 750 nm (in particular within a wavelength region smaller than or equal to 720 nm). Therefore, for example, a wavelength region of 650 nm to 720 nm can be used as a reference wavelength region for the transmitted light amount while regarding this wavelength region as a transparent region not having absorption for hemoglobin. In this embodiment, the wavelength region of 650 nm to 720 nm is defined as a wavelength region WR.

As described above, it is known that the absorbance $A_{W2}$ of hemoglobin in the wavelength region W2 decreases linearly depending on increase of oxygen saturation. Since the absorbance $A_{W7}$ of hemoglobin in the wavelength region W7 (the wavelength regions W4 to W6) can be regarded as a constant value regardless of oxygen saturation, a value of absorbance $A_{W2}$ with respect to absorbance $A_{W7}$ represents an index reflecting oxygen saturation. Specifically, an index X defined by the following equation (2) represents oxygen saturation.

$$X = A_{W2} - A_{W7} \quad (2)$$

Therefore, by obtaining the relationship between oxygen saturation and the index X experimentally in advance or by calculation, oxygen saturation can be estimated from the index X.

General Configuration of Electronic Endoscope System

Figure 4:
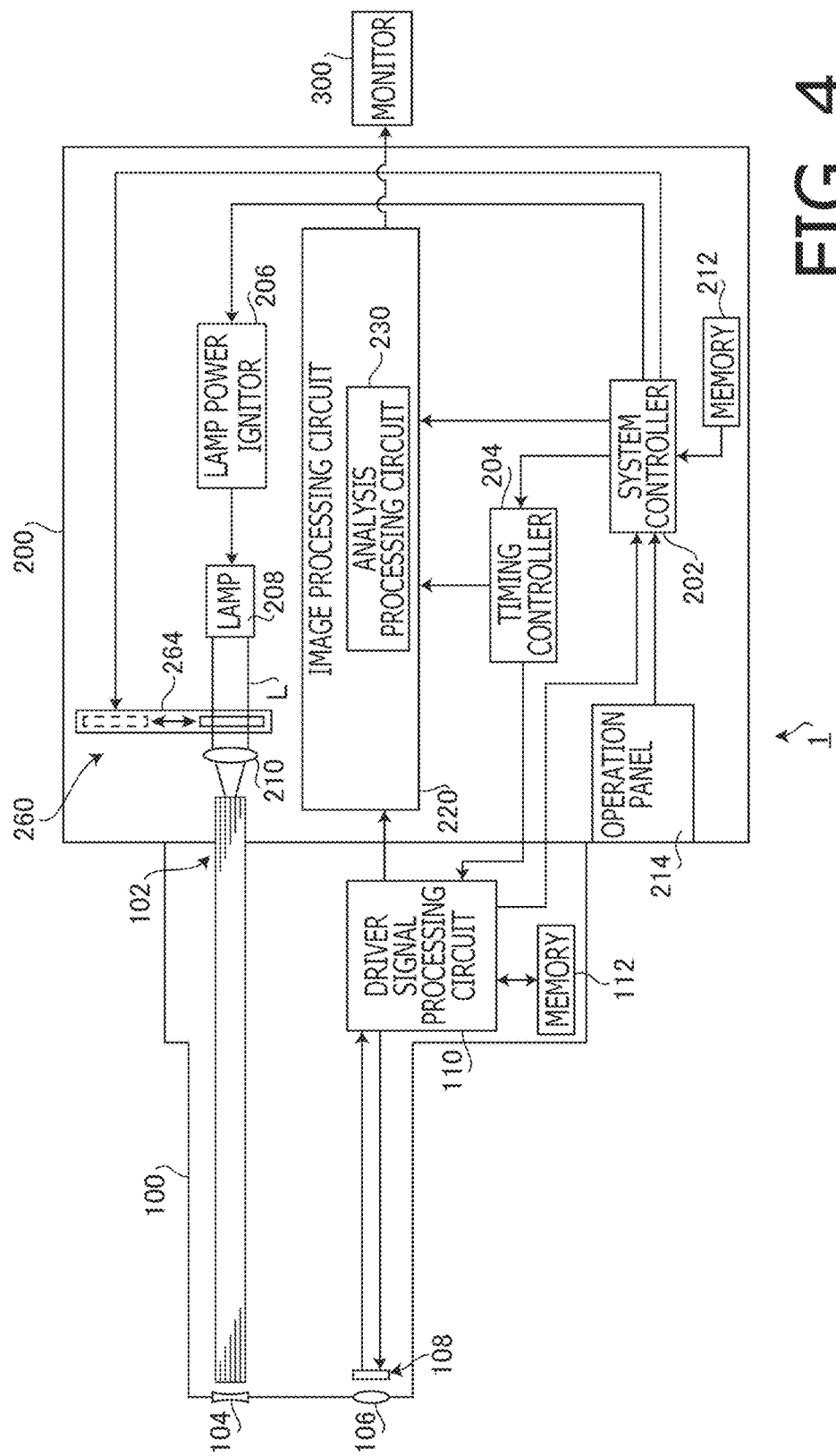
FIG. 4 is a block diagram illustrating a configuration of an electronic endoscope system according to an embodiment of the invention.

FIG. 4 is a block diagram illustrating a configuration of the electronic endoscope system 1 according to the embodiment. As shown in FIG. 4, the electronic endoscope system 1 includes an electronic scope 100, a processor 200 and a monitor 300.

The processor 200 includes a system controller 202, a timing controller 204, an image processing circuit 220, a lamp 208 and an optical filer device 260. The system controller 202 executes various programs stored in a memory 212, and controls totally the entire electronic endoscope system 1. The system controller 202 is connected to an operation panel 214. The system controller 202 changes operation of the electronic endoscope system 1 and parameters for operation of the electronic endoscope system 1. The timing controller 204 outputs clock pulses for adjusting timings of various types of operation to respective circuits in the electronic endoscope system 1.

The lamp 208 emits illumination light L after being activated by a lamp power igniter 206. For example, the lamp 208 is a high luminance lamp, such as, a xenon lamp, a halogen lamp, a mercury lamp or a metal halide lamp, or an LED (Light Emitting Diode). The illumination light L is light having a spectrum expanding principally from the visible light region to the invisible infrared region (or is white light including at least a visible light region).

Between the lamp 208 and a condenser lens 210, the optical filer device 260 is disposed. The optical filter device 260 includes a filer driving unit 264 and an optical filter 262 attached to the filer driving unit 264. The filer driving unit 264 is configured to be able to move the optical filter 262 between a position (indicated by a solid line) on an optical path of the illumination light L and a position (indicated by a dashed line) retracted from the optical path by causing the optical filer 262 to slide in a direction perpendicular to the optical path. It should be noted that the configuration of the filter driving unit 264 is not limited to the above described configuration, but the filter driving unit 264 may be configured such that the optical filter 262 is inserted into or drawn from the optical path of the illumination light L by rotating the optical filer 262 about a rotation axis which is shifted from the barycenter of the optical filter 262. The details about the optical filter 262 are explained later.

The electronic endoscope system 1 according to the embodiment is configured to be able to operate in three operation modes: a normal observation mode in which the white light emitted from the lamp 208 is used as the illumination light (normal light Ln) without change (or while removing an infrared component and/or a ultraviolet component) and endoscopic observation is conducted; a special observation mode in which filtered light Lf obtained by letting the white light pass the optical filter 262 is used as the illumination light and endoscopic observation is conducted; and a base line measurement mode in which a correction value used for the special observation mode is obtained. The optical filter 262 is disposed at the retracted position from the optical path in the normal observation mode, and is disposed on the optical path in the special observation mode.

The illumination light L (the filtered light Lf or the normal light Ln) which has passed the optical filter 260 is converged onto an entrance end face of an LCB (Light Carrying Bundle) 102 by the condenser lens 210, and is guided into the inside of the LCB 102.

The illumination light guided into the LCB 102 propagates through the LCB 102, and is emitted from an exit end face of the LCB 102 disposed in a tip portion of the electronic scope 100, and illuminates a subject via a light distribution lens 104. Light returning from the subject illuminated with the illumination light forms an optical image on a light-receiving surface of a solid state image pickup device 108 via an objective lens 106.

The solid state image pickup device 108 is a single chip color CCD (Charge Coupled Device) image sensor having a Bayer type pixel array. The solid state image pickup device 108 accumulates charges according to a light amount of an optical image converted at each pixel on the light-receiving surface, and generates and outputs an image signal (image data). The solid state image pickup device 108 has a so-called on-chip filter in which an R filter for letting red light pass therethrough, a G filter for letting green light pass therethrough and a B filter for letting blue light pass therethrough are directly formed on respective light receiving elements. The image signal generated by the solid state image pickup device 108 includes an image signal R captured by a light receiving element to which the R filter is attached, an image signal G captured by a light receiving element to which the G filter is attached and an image signal B captured by a light receiving element to which the B filter is attached.

Figure 5:
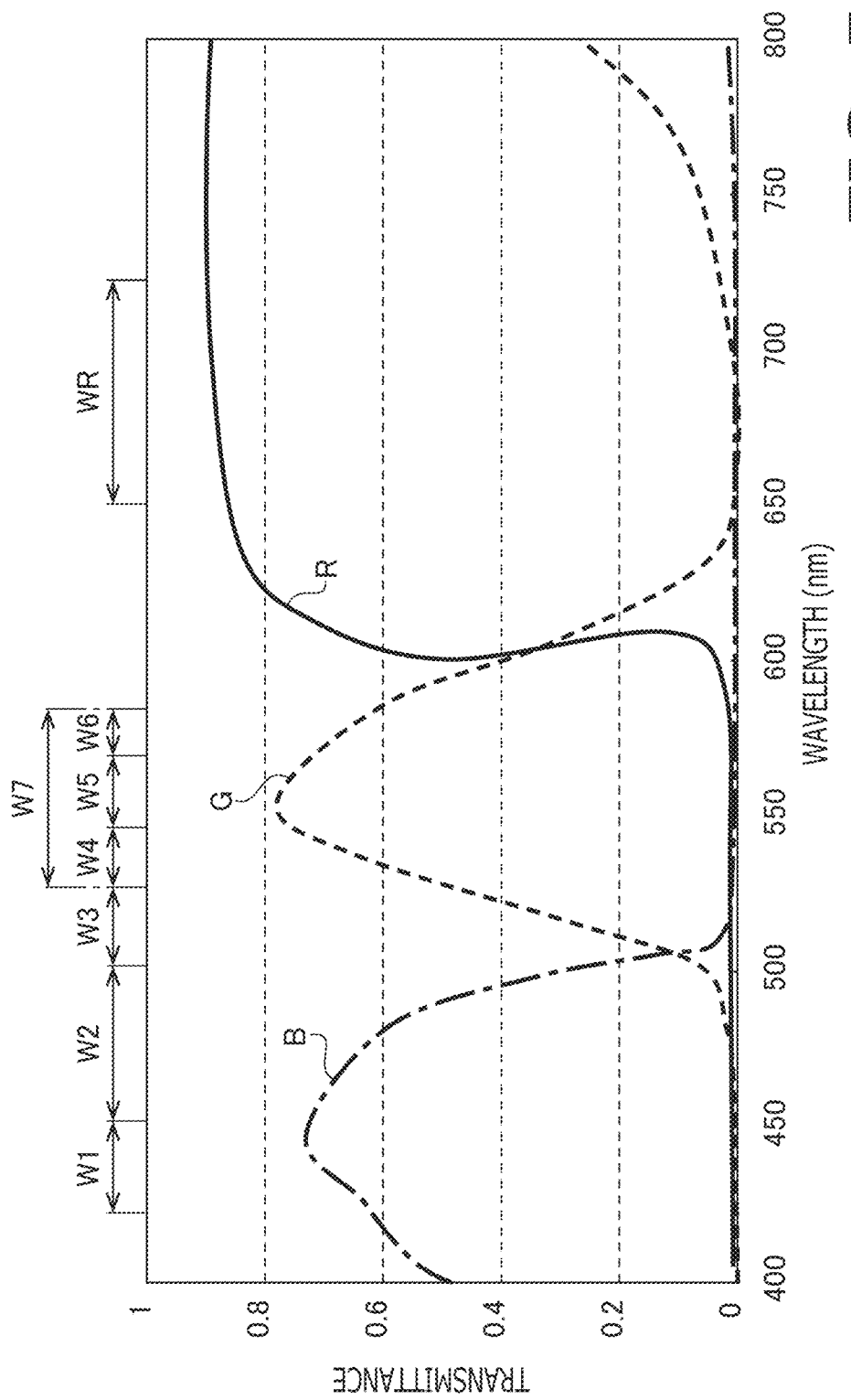
FIG. 5 illustrates a transmittance spectrum of a color filter of a solid state image pickup device.

FIG. 5 illustrates transmittance spectrums of the R filter, the G filter and the B filter of the solid state image pickup device 108. The R filter is a filter for letting light having a wavelength region of approximately 600 nm or more including the wavelength region WR pass therethrough. The G filter is a filter for letting light having a wavelength region of approximately 510 nm to 630 nm including the wavelength region W7 pass therethrough. The B filter is a filter for letting light having a wavelength region of approximately 510 nm or less including the wavelength regions of W1 and W2 pass therethrough. As described later, the optical filter 262 has the optical property where only light in the three wavelength regions WR, W7 and W2 is selectively allowed to pass therethrough. An optical image of light having the wavelength regions of WR, W7 and W2 which has passed through the optical filter 262 is then picked up by the light receiving elements of the solid state image pickup device 108 to which the R filter, the G filter and the B filter are attached, and is output as the image signals R, G and B.

The solid state image pickup device 108 is not limited to the CCD image sensor, but may be replaced with another type of image pickup devices, such as a CMOS (Complementary Metal Oxide Semiconductor) image sensor.

As shown in FIG. 4, in a connection part of the electronic scope 100, a driver signal processing circuit 110 is provided. To the driver signal processing circuit 110, an image signal is input from the solid state image pickup device 108 in a field cycle. The driver signal processing circuit 110 executes a predetermined process for the image signal input from the solid state image pickup device 108, and outputs the processed image signal to the image processing circuit 220 of the processor 200.

The driver signal processing circuit 110 accesses a memory 112 to read out unique information of the electronic scope 100. The unique information of the electronic scope 100 stored in the memory 112 includes, for example, sensitivity and the pixel number of the solid state image pickup device 108, operable field rates and a model number. The driver signal processing circuit 110 outputs the unique information read from the memory 112 to the system controller 202.

The system controller 202 executes various types of operation based on the unique information of the electronic scope 100, and generates control signals. By using the generated control signals, the system controller 202 controls the operation and timings of the various circuits in the processor 200 so that processes suitable for the electronic scope connected to the processor 200 are executed.

The timing controller 204 supplies clock pulses to the driver signal processing circuit 110 in accordance with the timing control by the system controller 202. In accordance with the clock pulses supplied from the timing controller 204, the driver signal processing circuit 110 drives and controls the solid state image pickup device 108 in synchronization with the field rate of video processed by the processor 200.

The image processing circuit 220 executes predetermined signal processing, such as color interpolation, a matrix operation and Y/C separation, and generates image data for monitor representation, and then converts the generated image data for monitor representation to a predetermined video format signal. The converted video format signal is output to the monitor 300. As a result, an image of the subject is displayed on a display screen of the monitor 300.

The image processing circuit 220 includes an analysis processing circuit 230. The analysis processing circuit 230 executes an analysis process The analysis processing circuit 230 executes a spectroscopic analysis process based on the obtained image signals R (Red), G (Green) and B (Blue) in the special observation mode, calculates an index value having correlation with oxygen saturation in a living tissue being the subject, and generates image data for visually displaying calculation results.

As described above, the electronic endoscope system 1 according to the embodiment is configured to be able to operate in the three operation modes including the normal observation mode where the white light (the normal light Ln) emitted from the lamp 208 is used as the illumination light, the special observation mode where spectroscopic analysis is executed using, as the illumination light, the filtered light Lf obtained by letting the white light pass the optical filter 262, and the base line measurement mode for obtaining the correction value for the special observation. Switching between the modes is executed by a user operation to an operation unit of the electronic scope 100 or the operation panel 214 of the processor 200.

In the normal observation mode, the system controller 202 controls the optical filter device 260 to retract the optical filter 262 from the optical path, and performs image-capturing by illuminating the subject with the normal light Ln. Then, the system controller 202 converts the image data obtained by the solid state image pickup device 108 to a video signal after subjecting the image data to image processing according to need, and displays an image corresponding to the image data on the monitor 300.

In the special observation mode and the base line measurement mode, the system controller 202 controls the optical filter device 260 to dispose the optical filter 262 on the optical path, and performs image-capturing by illuminating the subject with the filtered light Lf. Further, in the special observation mode, the analysis process which is described later is executed based on the image data obtained by the solid state image pickup device 108.

In the base line measurement mode, image-capturing is performed under illumination by the filtered light Lf using a color reference plate, such as, an achromatic diffusion plate or a standard reflector, and data to be used for a standardization process for the special observation mode which is described later is obtained.

The three primary color image data R(x, y), G(x, y) and B(x, y) obtained by using the filtered light Lf in the base line measurement mode is stored respectively, as base line image data $BL_R(x, y)$, $BL_G(x, y)$ and $BL_B(x, y)$, in an inside memory of the analysis processing circuit 230. It should be noted that each of R(x, y), G(x, y) and B(x, y) is a value of the image data at a pixel (x, y), and each of $BL_R(x, y)$, $BL_G(x, y)$ and $BL_B(x, y)$ is a value of the base line image data at a pixel (x, y). The pixel (x, y) is identified by a coordinate x in the horizontal direction and a coordinate y in the vertical direction.

Configuration and Property of Optical Filter

Figure 6:
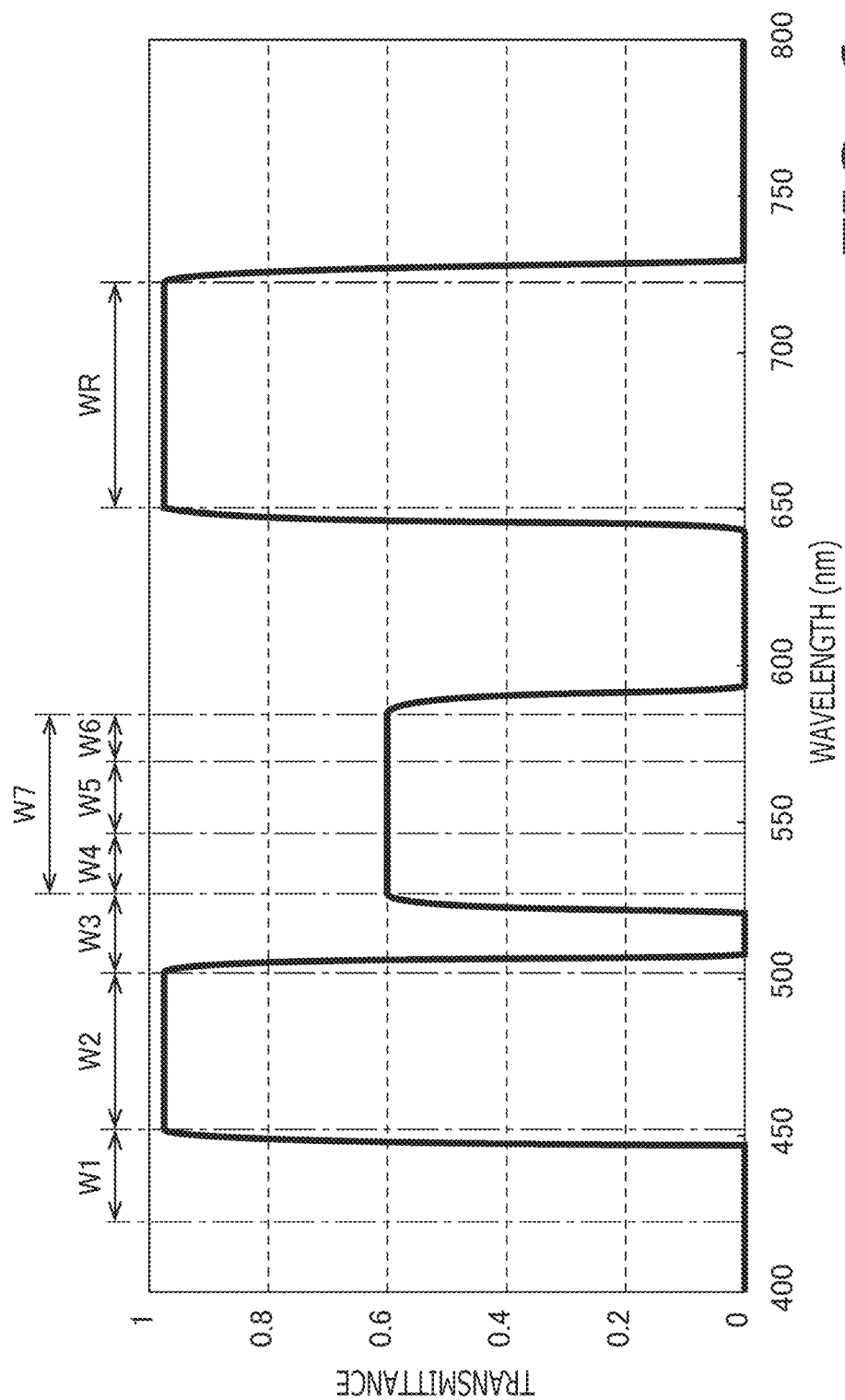
FIG. 6 illustrates a transmittance spectrum of an optical filter.

FIG. 6 illustrates a transmittance spectrum of the optical filter 262. The optical filter 262 is a so-called multi-peak dielectric multilayer filter having an optical property that only light of the three wavelength regions of W2, W7 and WR is selectively allowed to pass the optical filter 262 at least in the visible light wavelength region. The optical filter 262 has a flat transmittance in each of the wavelength regions W2, W7 and WR, and the transmittance in the wavelength region W7 is set to be lower than those of the other wavelength regions W2 and WR. This is because, since a light-emission spectrum of the white light source used in this embodiment has a peak in the wavelength region W7, the light amounts in the wavelength regions W2, W7 and WR after passing through the optical filter 262 can be maintained at approximately the same light amount in the wavelength regions W2, W7 and WR and thereby a noise level of the received light data can be kept constant. The transmittance property of the filter can be determined based on the spectral wavelength luminance property of an actually used light source and the sensitivity property of a light-receiving element. As the optical filter 262, another type of filter (e.g., an absorption type optical filter or an etalon filter in which a dielectric multilayer is used as a reflection coating of wavelength-selectivity) may be used.

Analysis Process in Special Observation Mode

Next, the analysis process executed in the special observation mode is explained.

Figure 7:
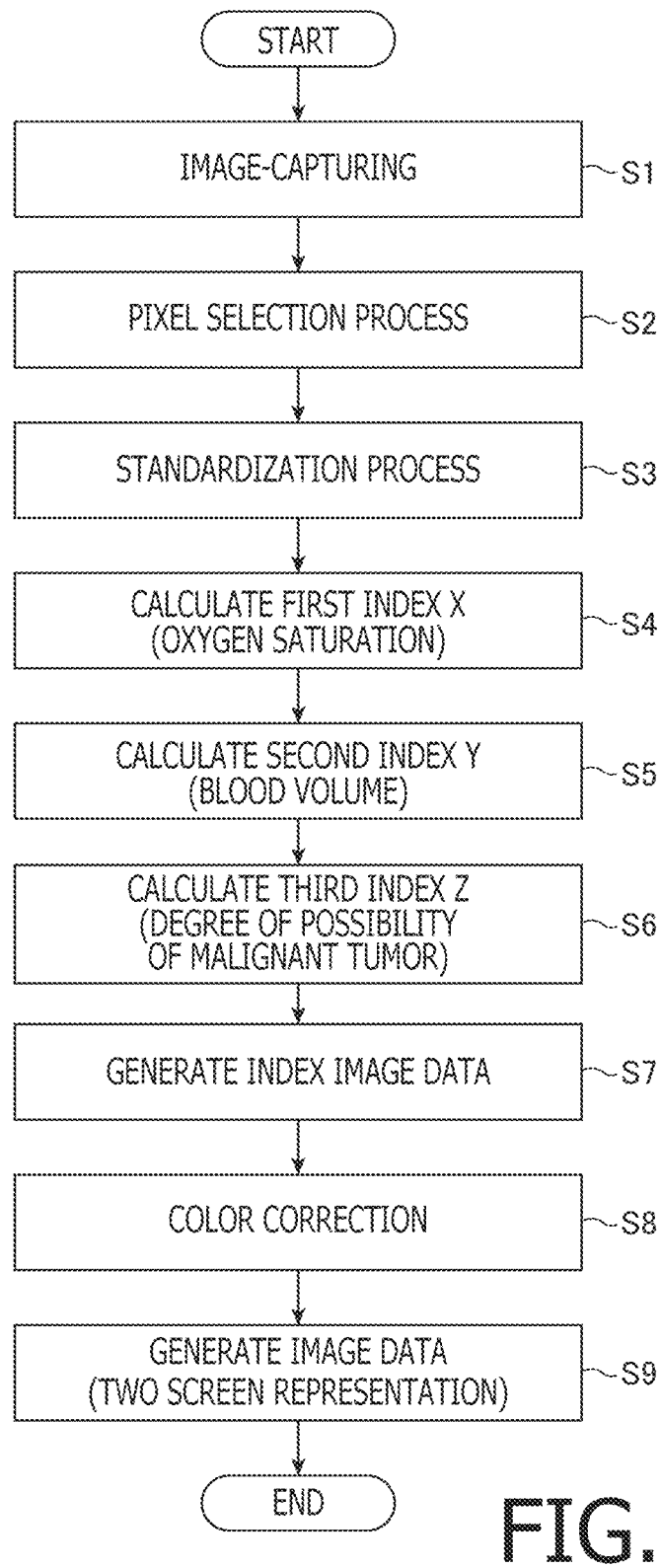
FIG. 7 is a flowchart illustrating an analysis process according to the embodiment.

FIG. 7 is a flowchart illustrating the analysis process. In the analysis process, first the subject is captured by the solid state image pickup device 108, and the analysis processing circuit 230 obtains the three primary color image data R(x, y), G(x, y) and B(x, y) generated by the solid state image pickup device 108 (S1).

Next, the analysis processing circuit 230 executes a pixel selection process S2 in which pixels (x, y) targeted for the following analysis process (S3 to S6) are selected by using the image data R(x, y), G(x, y) and B(x, y).

Regarding a portion not containing blood or a portion in which color of a tissue is dominantly affected by a substance other than hemoglobin, it is impossible to obtain a meaningful value even when oxygen saturation or blood volume is calculated from color of a pixel. Therefore, information from such a portion becomes noise. If such noise is calculated and is presented to a medical doctor, the noise not only becomes an obstacle to appropriate diagnosis, but also causes a harmful influence where a meaningless load is applied to the image processing circuit 220 and thereby the processing speed is decreased. For this reason, in an image generation process according to the embodiment, pixels (pixels in which the spectroscopic characteristic of hemoglobin is recorded) suitable for the analysis process are selected, and the analysis process is executed only for the selected pixels.

In the pixel selection process S2, only pixels satisfying all of the following conditions (3) to (5) are selected as target pixels for the analysis process.

$$B(x,y)/G(x,y) > a_1 \quad (3)$$

$$R(x,y)/G(x,y) > a_2 \quad (4)$$

$$R(x,y)/B(x,y) > a_3 \quad (5)$$

where a1, a2 and a3 are positive constants.

The above described three conditions are set based on the magnitude correlation of "G component<B component<R component" in the transmittance spectrum of blood. It should be noted that the pixel selection process S2 may be performed by using only one or two of the above described three conditions. For example, only the condition (4) and/or the condition (5) may be used to execute the pixel selection process S2 by focusing on red color unique to blood.

Next, the analysis processing circuit 230 executes a standardization process S3. The standardization process S3 according to the embodiment is a process for making it possible to perform quantitative analysis by correcting the optical property (e.g., transmittance of an optical filter or light-receiving sensitivity of an image pickup device) of the electronic endoscope system 1 itself.

In the standardization process, the analysis processing circuit 230 calculates standardization image data $R_S(x, y)$ by the following expression (6) using the image data R(x, y) obtained by using the filtered light Lf passed through the optical filter 262 and the base line image data $BL_R(x, y)$.

$$R_S(x,y) = R(x,y)/BL_R(x,y) \quad (6)$$

Similarly, from the following expressions (7) and (8), standardization image data $G_S(x, y)$ and $B_S(x, y)$ is calculated.

$$G_S(x,y) = G(x,y)/BL_G(x,y) \quad (7)$$

$$B_S(x,y) = B(x,y)/BL_B(x,y) \quad (8)$$

Although, in the following explanation, the standardization image data $R_S(x, y)$, $G_S(x, y)$ and $B_S(x, y)$ is used; however, calculation for the index may be performed by using the image data R(x, y), G(x, y) and B(x, y) in place of the standardization data $R_S(x, y)$, $G_S(x, y)$ and $B_S(x, y)$ without executing the standardization process.

Next, the analysis processing circuit 230 calculates a first index X having a correlation with oxygen saturation by the following expression (9) (S4).

$$X = B_S(x,y)/G_S(x,y) \quad (9)$$

The image data G(x, y) represents an optical image formed by light in the wavelength region W7 which has passed through the optical filter 262. The image data B(x, y) represents an optical image formed by light in the wavelength region W2 which has passed through the optical filter 262. As described above, the reflectivity of a living tissue with respect to light in the wavelength region W2 (i.e., a value of the image data B) depends on both of oxygen saturation and a total hemoglobin amount. On the other hand, the reflectivity of a living tissue with respect to light in the wavelength region W7 (i.e., a value of the image data G) does not depend on oxygen saturation, but depends on a total hemoglobin amount. By dividing the standardization reflectivity $B_S$ (a value of the image data B after correction) by the standardization reflectivity $G_S$ (a value of the image data G after correction), it becomes possible to cancel out contribution by a total hemoglobin amount. Furthermore, through such division, contribution by an incident angle of the illumination light IL (the filtered light Lf) with respect to a living tissue or a surface condition of a living tissue can also be cancelled out, and thereby only contribution by oxygen saturation can be extracted. Therefore, the first index X becomes a suitable index for representing oxygen saturation.

Next, the analysis processing circuit 230 calculates a second index Y having correlation with the blood volume in a living tissue (a total hemoglobin amount) from the following expression (10) (S5).

$$Y=G_S(x,y)/R_S(x,y) \quad (10)$$

As described above, the standardization reflectivity $G_S$ does not depend on oxygen saturation but depends on a total hemoglobin amount. On the other hand, since the standardization reflectivity $R_S$ (a value of the image data R after correction) is reflectivity of a living tissue in the wavelength region WR in which there is almost no absorption for hemoglobin, the standardization reflectivity $R_S$ does not depend on oxygen saturation nor on a total hemoglobin amount. By dividing the standardization reflectivity $G_S$ by the standardization reflectivity $R_S$, contribution to reflectivity of a living tissue by an incident angle of the illumination light IL to a living tissue or a surface condition of a living tissue can be canceled out, and thereby only contribution to a total hemoglobin amount can be extracted. Therefore, the second index Y becomes a suitable index for a total hemoglobin amount.

Next, the analysis processing circuit 230 calculates a third index Z representing a possibility of a malignant tumor based on the first index X and the second index Y.

It is known that a tissue of a malignant tumor has a larger amount of total hemoglobin than a normal tissue by vascularization, and oxygen saturation in a tissue of a malignant tumor is lower than that of a normal tissue since metabolism of oxygen in a tissue of a malignant tumor is remarkable. For this reason, the analysis processing circuit 230 extracts a pixel having the first index X representing oxygen saturation calculated by the expression (9) is smaller than a predetermined reference value (a first reference value) and the second index Y representing a total hemoglobin amount calculated by the expression (10) larger than a predetermined reference value (a second reference value), and assigns "1" representing a possibility of a malignant tumor to the third index Z of the extracted pixel and assigns "0" to the third indexes X of the other pixels.

Each of the first index X, the second index Y and the third index Z may be defined as a binary index, and the third index Z may be calculated as a logical product or a logical sum of the first index X and the second index Y. In this case, for example, by defining X=1 (low oxygen saturation) when the right term of the expression (9) is smaller than a predetermined value, defining X=0 (a normal value) when the right term of the expression (9) is larger than or equal to the predetermined value, defining Y=1 (large blood volume) when the right term of the expression (10) is larger than or equal to a predetermined value and defining Y=0 (a normal value) when the right term of the expression (10) is smaller than the predetermined value, Z can be calculated as Z=X·Y (logical product) or Z=X+Y (logical sum).

The foregoing is an example where the third index Z is defined as a binary index; however, the third index Z may be defined as a multiple value (or as a continuous value) index representing a degree of possibility of a malignant tumor. In this case, the third index Z(x, y) representing a degree of possibility of a malignant tumor may be calculated based on a deviation from the first reference value or an average of the first index X(x, y) and a deviation from the second reference value or an average of the second index Y(x, y). For example, the third index Z(x, y) may be calculated as a sum or a product of the deviation of the first index X(x, y) and the deviation of the second index Y(x, y).

Next, the analysis processing circuit 230 generates index mage data in which one of the first index X(x, y), the second index Y (x, y) and the third index Z(x, y) is designated in advance by a user as a pixel value (luminance) (S7). It should be noted that in step S7 index image data for all the first index X(x, y), the second index Y (x, y) and the third index Z(x, y) may be generated.

Next, the analysis processing circuit 230 executes a color correction process S8 for the image data R(x, y), G(x, y) and B(x, y). Since the filtered light Lf which has passed through the optical filter 262 includes the three primary color spectrum components of R (the wavelength region WR), G (the wavelength region W7) and B (the wavelength region W2), it is possible to obtain a color image using the filtered light Lf. However, since the band of the spectrum of the filtered light Lf is restricted, an image captured by using the filtered light Lf has a relatively unnatural tone of color in comparison with an image captured by using the normal light Ln. For this reason, in this embodiment, the color correction process S8 is executed for the image data R(x, y), G(x, y) and B(x, y) obtained by using the filtered light Lf so that a tone of color of an image captured by using the filtered light Lf approaches a tone of color of an image captured by using the normal light Ln.

The color correction process S8 is executed, for example, by adding correction values $C_R$, $C_G$ and $C_B$ obtained in advance to the image data R(x, y), G(x, y) and B(x, y) or multiplying the image data R(x, y), G(x, y) and B(x, y) by the correction values $C_R$, $C_G$ and $C_B$. Alternatively, by preparing a color matrix Mf for the filtered light Lf in addition to a color matrix Mn for the normal light Ln, the color collection may be performed through a color matrix operation. The correction values $C_R$, $C_G$ and $C_B$ and the color matrix Mf are set in advance based on image data which the electronic endoscope system 1 obtains by capturing a color reference plate illuminated with the filtered light Lf, and are stored in the inside memory of the analysis processing circuit 230. The analysis process may be configured to omit the color correction process S8.

Next, the analysis processing circuit 230 generates image data for displaying on the monitor 300 based on the image data subjected to the color correction process S8 and the index image data generated in step S7 and the like (S9). In an image data generation process S9, various types of image data for, for example, multiple image representation in which an endoscopic image after color correction and one or more types of index images are displayed side by side on one screen, endoscopic image representation in which only an endoscopic image after color correction is displayed, and index image representation in which only one or more types of index images designated by the user is displayed, may be generated. The type of image data to be generated is selected by a user operation to the operation unit of the electronic scope 100 or to the operation panel 214 of the processor 200. Furthermore, related information, such as, patient information, input from, for example, the operation panel 214 of the processor 200 is displayed on the display screen in a superimposing manner.

Figure 8A:
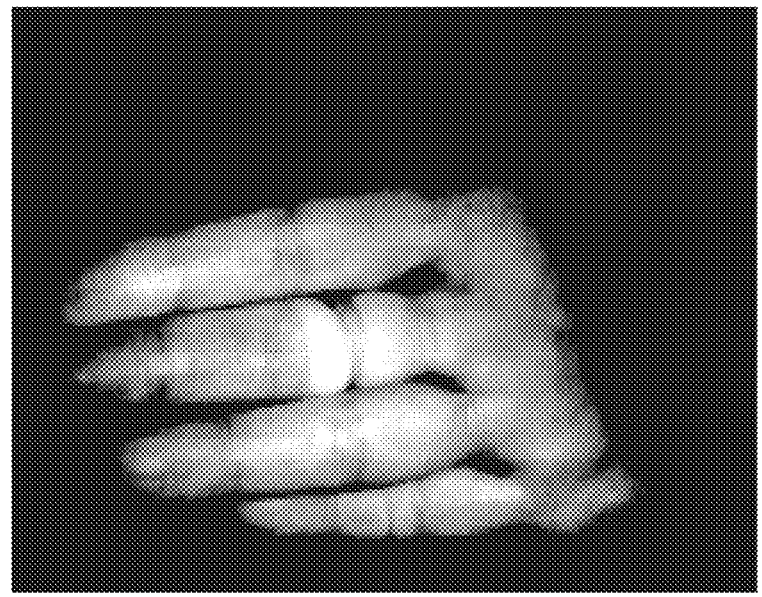
Figure 8B:
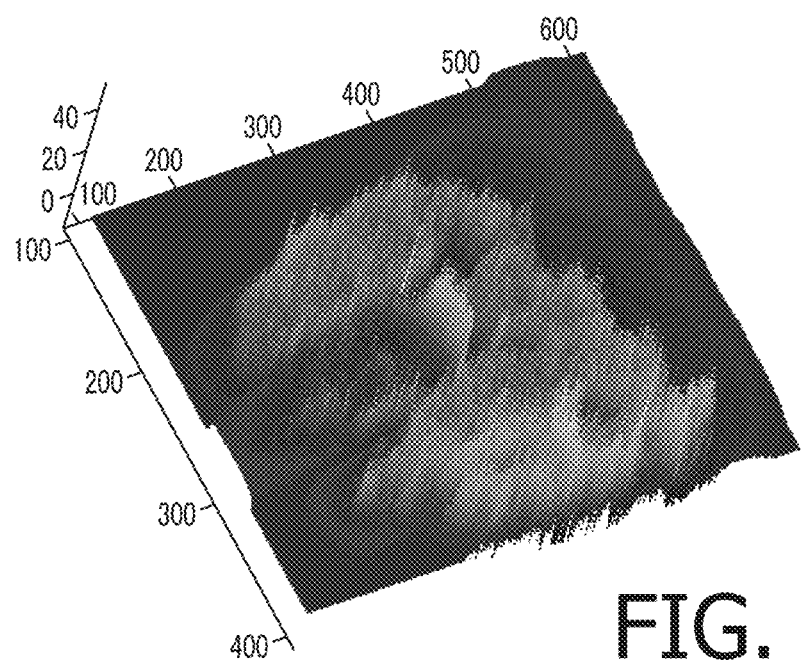

FIGS. 8A and 8B are examples displayed on the monitor 300. Specifically, FIG. 8A is an endoscopic image, and FIG. 8B is an index image of the first index X(x, y). Each of FIGS. 8A and 8B is obtained by observing the right hand in a state where a portion around a proximal interphalangeal joint of the middle finger is pressed by a rubber band. FIG. 8B shows a state where oxygen saturation becomes lower in a distal part with respect to the pressed part of the right middle finger due to hampering of blood flow by pressure. Furthermore, it can be read that, on a proximal side immediately near the pressed part, arterial blood stays and therefore oxygen saturation becomes high locally.

By conducting endoscopic observation while displaying two screens including an endoscopic image and an index image on the monitor 300 in the special observation mode, it becomes possible to securely find a malignant tumor showing characteristic change in a total hemoglobin amount and oxygen saturation. Furthermore, when a portion having a possibility of a malignant tumor is found, by switching from the special observation mode to the normal observation mode through an operation to the electronic scope 100 and thereby displaying a normal observation image having proper color reproducibility on the entire screen, more delicate diagnosis can be conducted. The electronic endoscope system 1 according to the embodiment is configured to be able to switch between the normal observation mode and the special observation mode easily and rapidly by simply changing an image processing manner while inserting or retracting the optical filter 262 to or from the optical path by an operation to the electronic scope 100.

Furthermore, in the electronic endoscope system 1, the multi-peak optical filter 262 which divides light into the three wavelength regions W2, W7 and WR is employed, and further the configuration where light of the three wavelength regions W2, W7 and WR respectively passes the B filter, the G filter and the R filter of the solid state image pickup device 108 is employed. With this configuration, it becomes possible to generate a frame of endoscopic image and an index image by capturing one frame (2 fields). Accordingly, a video image having a high effective frame rate can be obtained.

Figure 9:
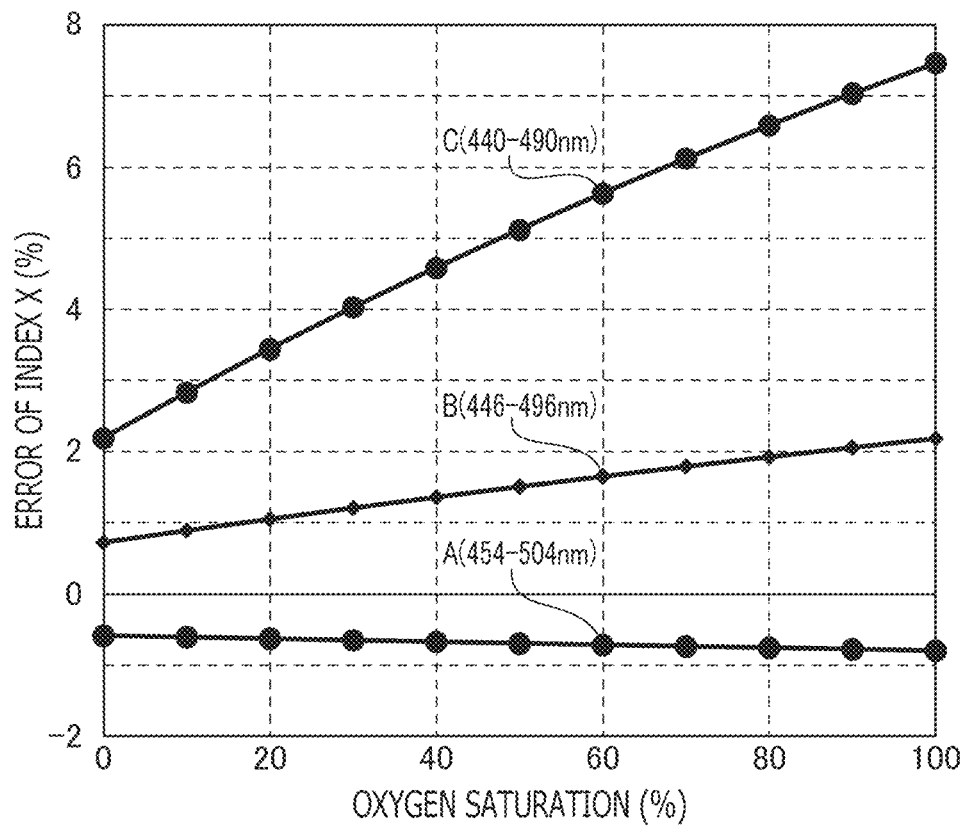
FIG. 9 is a graph plotting results of simulation in which errors of an index X caused when a transmittance wavelength region of the optical filter corresponding to the wavelength region W2 is shifted are simulated.

The three transmittance wavelength regions of the optical filter 262 may be shifted somewhat from the wavelength regions W2, W7 and WR defined by the isosbestic points of hemoglobin as long as the indexes X and Y having a desired degree of accuracy can be obtained. FIG. 9 is a graph plotting results of simulation in which errors of the index X caused when the transmittance wavelength region of the optical filter 262 corresponding to the wavelength region W2 (452 nm to 502 nm) is shifted are simulated. In FIG. 9, the horizontal axis represents oxygen saturation, and the vertical axis represents an error of the index X.

In FIG. 9, a plotted point A represents an error caused when the optical filter 262 configured to let light of a wavelength region of 454 nm to 504 nm shifted to the longer wavelength side by 2 nm from the wavelength region W2 pass therethrough is used. A plotted point B represents an error caused when the optical filter 262 configured to let light of a wavelength region of 446 nm to 496 nm shifted to the shorter wavelength side by 6 nm from the wavelength region W2 pass therethrough is used. A plotted point C represents an error caused when the optical filter 262 configured to let light of a wavelength region of 440 nm to 490 nm shifted to the shorter wavelength side by 12 nm from the wavelength region W2 pass therethrough is used. The error of each of the plotted points is smaller than 8%. Furthermore, it is understood that the graph shows a tendency that the error becomes a little larger in the case where the transmittance wavelength region is shifted to the longer wavelength side relative to the case where the transmittance wavelength region is shifted to the shorter wavelength side.

It is reported that oxygen saturation in a normal living tissue is larger than or equal to approximately 90%, and, by contrast, oxygen saturation in a malignant tumor is smaller than or equal to approximately 40%. Therefore, it is considered that, if the error of the index X is suppressed to be smaller than or equal to approximately ±5%, the index becomes sufficiently usable in practical use for the purpose of identifying a malignant tumor.

Therefore, regarding the shift amount of the transmittance wavelength region of the optical filter 262 corresponding to the wavelength region W2, a range of ±12 nm (or a range of −12 nm to +10 nm, considering that the error becomes larger when the transmittance wavelength region shifts to the longer wavelength side) is sufficiently acceptable. At least in a range of the plotted condition in FIG. 9 (i.e., in the range of the wavelength shift amount of −12 nm to +2 nm), the error of the index X can be suppressed to a sufficiently usable range in practical use.

Furthermore, although FIG. 9 shows simulation results when the wavelength is shifted without changing the wavelength width; however, it is considered that substantially the same tolerance can be applied to shift of the wavelength region accompanying increase or decrease of a wavelength width. That is, it is considered that an error within a range of ±12 nm (preferably, −12 nm to +10 nm, and more preferably, −12 nm to +2 nm) is allowed for each of a longer wavelength edge and a shorter wavelength edge of a transmittance wavelength region corresponding to the wavelength region W2.

Furthermore, it is considered that, regarding the wavelength region corresponding to each of the wavelength region W7 and the wavelength region WR, at least substantially the same tolerance can be accepted.

According to the above described embodiment, a relatively wide wavelength region having a property that absorption of the entire wavelength region does not depend on oxygen saturation is used in place of an isosbestic point of which wavelength region is extremely narrow. Therefore, it becomes unnecessary to use light having an extremely narrow band and having a high spectral energy density, such as laser, and it becomes possible to accurately estimate information concerning hemoglobin density (blood density) without being affected by oxygen saturation even when narrowband light having a low spectral energy density, such as, light whose wavelength region is separated from white light by a bandpass filter, is used.

The foregoing is the explanation about the embodiments of the invention. The invention is not limited to the above described embodiments, but can be varied in various ways within the scope of the invention. For example, the invention includes a combination of embodiments explicitly described in this specification and embodiments easily realized from the above described embodiment.

In the above described embodiment, the example where the wavelength region W2 is used as a wavelength region for blue color used for the special observation mode is described; however, the wavelength region W1 may be used in place of the wavelength region W2. The wavelength region W1 has a property that a difference between absorption of oxyhemoglobin and absorption of deoxyhemoglobin is larger than that of the wavelength region W2. Therefore, by using the wavelength region W1, it becomes possible to detect change in oxygen saturation with higher sensitivity.

On the other hand, the wavelength region W2 has a property that absorption of hemoglobin is smaller than that of the wavelength region W1, and, when a xenon lamp is used as the lamp 208, the light emission intensity of the lamp 208 becomes higher and therefore a larger light amount can be obtained. For this reason, by using the wavelength region W2, it becomes possible to detect oxygen saturation with a high degree of accuracy (with low noise).

The above described embodiment is an example where a spectroscopic analysis result is displayed as an gray scale index image or a monochrome index image; however, the displaying manner of analysis result is not limited to such an example. For example, the image data R(x, y), G(x, y) and B(x, y) may be altered depending on the index value. For example, for a pixel whose index value exceeds a reference value, a process for increasing the brightness of the pixel, a process for changing color phase of the pixel (e.g., a process for intensifying redness by increasing a red component or a process for rotating color phase by a predetermined angle), or a process for blinking the pixel (or a process for periodically changing color phase) may be performed.

In the above described embodiment, the solid state image pickup device 108 is explained as a solid state image pickup device for capturing a color image having an on-chip color filter; however, the present invention is not limited to such a configuration. For example, a solid state image pickup device for capturing a monochrome image having a so-called frame sequential type color filter may be used. The color filter may be disposed at any point on the optical path extending from the lamp 208 to the solid state image pickup device 108.

In the above described embodiment, the optical filter device 260 is disposed on the light source side to filter the illumination light IL; however, the present invention is not limited to such a configuration. The optical filter 260 may be disposed on an image pickup device side, and filtering may be performed for returning right from the subject.

In the above described embodiment, the present invention is applied to an electronic endoscope system which is an example of a digital camera; however, the present invention may be applied to a system in which another type of digital camera (e.g., a digital single-lens reflex camera or a digital video camera) is used. For example, when the present invention is applied to a digital still camera, observation for a body surface tissue and observation (e.g., rapid examination for brain blood volume) for a brain tissue during craniotomy can be conducted.

This application claims priority of Japanese Patent Application No. P2014-179036, filed on Sep. 3, 2014. The entire subject matter of the application is incorporated herein by reference.

What is claimed is:

1. An image capturing system, comprising:
a light source device that emits illumination light containing a plurality of wavelength regions spaced from each other and not overlapping with each other;
an image pickup device that generates image data by capturing an image of a living tissue as a subject illuminated with the illumination light, the image pickup device having an RGB filter, the plurality of wavelength regions comprising a first wavelength region corresponding to a B filter of the RGB filter, and a second wavelength region corresponding to a G filter of the RGB filter; and
an image processor configured to calculate a first index representing a molar concentration ratio of a first biological substance and a second biological substance contained in the living tissue based on the image data which includes information on the first wavelength region and the second wavelength region obtained by the image pickup device in a single frame,
wherein:
in the first wavelength region, a value of image data B of the living tissue captured by a light-receiving element of the image pickup device to which the B filter is attached varies depending on the molar concentration ratio;
the second wavelength region contains a plurality of isosbestic points of the living tissue, and, in the second wavelength region, a value of image data G of the living tissue captured by a light-receiving element of the image pickup device to which the G filter is attached has a constant value independent of the molar concentration ratio; and
the image processor is configured to calculate the first index representing the molar concentration ratio based on the image data B and the image data G.

2. The image capturing system according to claim 1, wherein the light source device comprises:
a white light source; and
an optical filter that separates the illumination light from white light emitted by the white light source.

3. The image capturing system according to claim 1, wherein the first index is defined as a value obtained by dividing the image data B by the image data G.

4. The image capturing system according to claim 1, wherein:
the plurality of wavelength regions comprise a third wavelength region corresponding to an R filter of the RGB filter;
absorbance of the living tissue in the third wavelength region is substantially zero; and
the image processor is configured to calculate a second index having correlation with a sum of molar concentrations of the first biological tissue and the second biological tissue based on the image data G and image data R of the living tissue captured by a light-receiving element of the image pickup device to which the R filter is attached.

5. The image capturing system according to claim 4, wherein the second index is defined as a value obtained by dividing the image data G by the image data R.

6. The image capturing system according to claim 4, further comprising a memory that stores base line image data $BL_R$, $BL_G$ and $BL_B$ respectively corresponding to image data of R, G and B colors obtained by capturing a color reference plate illuminated with the illumination light.

7. The image capturing system according to claim 6, wherein the image processor is configured to calculate the first index and the second index by using, as the image data R, the image data G and the image data B, standardization image data $R_S$, $G_S$ and $B_S$ defined by following expressions:

$$R_S = R/BL_R$$

$$G_S = G/BL_G$$

$$B_S = B/BL_B.$$

8. The image capturing system according to claim 1, wherein the image processor is configured to generate first index image data representing distribution of the first index in the living tissue.

9. The image capturing system according to claim 8, wherein the first index image data is image data having a pixel value being the first index.

10. The image capturing system according to claim 1, wherein:
the first biological substance is oxyhemoglobin;
the second biological substance is deoxyhemoglobin; and
the first index has correlation with oxygen saturation.

11. The image capturing system according to claim 4, wherein the image processor is configured to calculate a third index representing a degree of possibility of a malignant tumor of the living tissue based on the first index and the second index.

12. The image capturing system according to claim 11, wherein, for a pixel having the first index lower than a first reference value and the second index higher than a second reference value, a value representing a high possibility of a malignant tumor is assigned to the third index.

13. The image capturing system according to claim 1, wherein the second wavelength region is comparted by a first pair of isosbestic points of the living tissue, and includes a second pair of isosbestic points of the living tissue lying within a range defined by the first pair of isosbestic points.

14. An electronic endoscope system, comprising:
the image capturing system according to claim 1; and
an electronic endoscope provided with the image pickup device.

15. The electronic endoscope system according to claim 14, wherein the system is operable in three operation modes including a normal observation mode in which white light emitted from a lamp of the light source device is used as the illumination light, a special observation mode in which spectroscopic analysis is performed using, as the illumination light, filtered light obtained by white light that has passed through an optical filter and a baseline measurement mode by which a correction value is obtained for the spectroscopic analysis of the special observation mode.

16. The electronic endoscope system according to claim 14, wherein the plurality of wavelength regions comprise a third wavelength region corresponding to an R filter of the RGB filter;
absorbance of the living tissue in the third wavelength region is substantially zero; and
the image processor is configured to calculate a second index having correlation with a sum of molar concentrations of the first biological tissue and the second biological tissue based on the image data G and the image data R of the living tissue captured by a light receiving element of the image pickup device to which the R filter is attached.

17. The electronic endoscope system according to claim 16, wherein the second index is comprises a value obtained by dividing the image data G by the image data R.

18. The electronic endoscope system according to claim 16, further comprising a memory that stores baseline image data $BL_R$, $BL_G$, and $BL_B$ respectively corresponding to the image data of R, G, and B colors obtained by capturing a color reference plate illuminated with the illumination light.

19. The electronic endoscope system according to claim 16, wherein the image processor is configured to calculate a third index representing a degree of possibility of a malignant tumor of the living tissue based on the first index and the second index.

20. The electronic endoscope system according to claim 16, wherein the first biological substance is oxyhemoglobin, the second biological substance is deoxyhemoglobin and the first index has a correlation with oxygen saturation.

* * * * *